US006774228B1

(12) United States Patent
Parker et al.

(10) Patent No.: US 6,774,228 B1
(45) Date of Patent: Aug. 10, 2004

(54) TETRA-AZA MACROCYCLES AND METAL COMPLEXES THEREOF

(75) Inventors: David Parker, Durham (GB); Thomas Andrew Millican, Maidenhead (GB)

(73) Assignee: Celltech Limited, Berkshire (GB)

(*) Notice: Subject to any disclaimer, the term of this patent is extended or adjusted under 35 U.S.C. 154(b) by 1826 days.

(21) Appl. No.: 07/577,072

(22) Filed: Aug. 31, 1990

Related U.S. Application Data

(63) Continuation of application No. 07/372,348, filed as application No. PCT/GB88/00671 on Aug. 12, 1988, now abandoned.

(30) Foreign Application Priority Data

Aug. 12, 1987 (GB) .............................. 8819042

(51) Int. Cl.[7] ........................ C07D 257/02; C07F 1/06; C07F 5/00; A61B 5/055

(52) U.S. Cl. ................. 540/474; 530/391.1; 530/391.5; 424/9.363

(58) Field of Search ................................ 540/465, 474; 534/15, 16; 530/409, 387.1, 391.5; 536/17.1, 17.4, 24

(56) References Cited

U.S. PATENT DOCUMENTS

| | | | | |
|---|---|---|---|---|
| 4,174,319 A | | 11/1979 | Kobuke ..................... | 260/239 |
| 4,174,428 A | * | 11/1979 | Tabushi et al. ............. | 540/465 |
| 4,432,907 A | | 2/1984 | Wieder et al. .............. | 436/500 |
| 4,472,509 A | | 9/1984 | Gansow et al. ............. | 436/548 |
| 4,659,839 A | | 4/1987 | Nicolotti et al. ........... | 548/546 |
| 4,671,958 A | | 6/1987 | Rodwell et al. ............. | 514/2 |
| 4,678,667 A | | 7/1987 | Meares et al. .............. | 424/85 |
| 4,702,998 A | | 10/1987 | Tanaka et al. .............. | 540/474 |
| 4,877,600 A | * | 10/1989 | Bonnemain et al. ........ | 514/184 |
| 4,885,363 A | | 12/1989 | Tweedle et al. ............ | 540/465 |
| 4,923,985 A | * | 5/1990 | Gansow ...................... | 540/474 |
| 5,049,667 A | * | 9/1991 | Schaefer et al. ............ | 540/474 |
| 5,053,503 A | * | 10/1991 | Dean et al. ................. | 540/475 |
| 5,428,154 A | * | 6/1995 | Gansow ...................... | 540/474 |
| 2003/0108486 A1 | * | 6/2003 | Platzek et al. ............. | 540/474 |

FOREIGN PATENT DOCUMENTS

| | | | |
|---|---|---|---|
| AU | 76267/87 | 2/1988 | |
| AU | 14611/88 | 10/1988 | ................ 540/465 |
| AU | 18332/88 | 1/1989 | ................ 540/465 |
| EP | 0173629 | 8/1985 | |
| EP | 0188256 | 7/1986 | |
| EP | 0232751 | 8/1987 | |
| EP | 0 255 471 | 1/1988 | ................ 540/465 |
| EP | 0255471 | 2/1988 | |
| SU | 1098937 | * 6/1984 | ................ 540/474 |
| SU | 8518012 | * 6/1984 | ................ 540/474 |
| WO | WO88/08422 | 11/1988 | ................ 540/465 |
| WO | WO 89/00557 | 1/1989 | ................ 540/465 |
| WO | 89/01476 | 2/1989 | |

OTHER PUBLICATIONS

Moi, et al Analytical Biochemistry 148, 249–53 1985.*
Gansow, et al. Radionuclide Generators, ACS Symposium Series 1984: No. 241, pp. 215–227.*
Benjamini, et al. Immunology, A Short Course [New York; J. Wiley and Sons, 1991] pp. 38 to 39.*
Khaw et al., *Science.* 209, 295 (1980).
Krejcarek et al. *Biochem. Biophys. Res. Comm.,* 77, 581 (1977).
Childs, R.L. and Hnatowich, D.J., *J. Nuc. Med.* 26, 293 (1985).
Stetter, H., et al., *Angew. Chem. Int. Ed. Engl.,* 15, 686 (1976).
Loncin, J.F., et al., *Inorg. Chem.,* 25, 2646 (1986).
Moi, C.F., et al., *J. Am. Chem. Soc.,* 110, 6266 (1988).
Tweedle, M.F., et al., *J. Nuc. Med.,* 28, 705 (1988).
Goodwin, C.H., et al., *J. Nuc. Med.,* 27, 959 (1986).
Paik, C.H., et al., *J. Nuc. Med.,* 28, 572 (1987).
Paik, C.H., et al., *J. Nuc. Med.,* 29, 889 (1988).
Haseman, C.F., et al., *Eur. J. Nuc. Med.,* 12, 455 (1986).
Parker et al., *Pure & Appl. Chem.,* vol. 61, No. 9, 1637–1641 (1989).
Craig et al., *J. Chem. Soc. Chem. Commun.* (1989), pp. 794–796.
Cox et al., *J. Chem. Soc. Chem. Commun.* (1989), pp. 797–798.
Paik et al., *J. Nucl. Sci.,* vol. 30, No. 10, p. 1693–1701 (10/89).
Paik et al., *Nucl. Med. Biol.,* vol. 16, No. 5, pp. 475–481 (1989).
Deshpande et al., *Nucl. Med. Biol.,* vol. 16, No. 6, pp. 587–597 (1989).
Deshpande et al., *The Journal of Nuclear Medicine.* "Copper–67–Labeled Monoclonal Antibody Lym–1, A Potential Radiopharmaceutical for Cancer Therapy: Labeling and Biodistribution in RAJI Tumored Mice", vol. 29, No. 2, pp. 217–225 (Feb. 1988).
Franz, J., et al., Abstract from Journal of Nuclear Medicine, Abstract No. 553, vol. 26, No. 5 (May 1985).
Franz et al., poster exhibited at 32nd Annual Meeting of the Society of Nuclear Medicine prior to May 1985.
Meares, Claude F., Protein Tailoring for Food and Medicine Uses edited by R.E. Feeny et al., *Attaching Metal Ions to Antibodies,* pp. 339–352 (1986).

(List continued on next page.)

Primary Examiner—Mark L. Berch
(74) Attorney, Agent, or Firm—Mathews, Collins, Shepherd & McKay, P.A.

(57) ABSTRACT

1,4,7,10-Tetrazacyclododecanes carrying a side chain terminating in a group capable of reacting with an antibody, and their complexes with a di- or tripositive metal having a coordination number of 6 or more can be used to prepare imaging agents. Typical metals are indium, copper, lead, bismuth, yttrium, terbium, gadolinium, and scandium. The compounds can be reacted with a monoclonal or polyclonal antibody or antibody fragment to target the metal to a specific type of tissue.

6 Claims, No Drawings

OTHER PUBLICATIONS

Goodwin, D.A., et al., Abstract of *"In Complex of a New Macrocyclic Bifunctional Chelator TETA"*, presented at European Nuclear Medicine Congress Meeting at Barbican, London, Sep. 3–6 (1985).
Meares et al., Int. J. Cancer Suppl., 2, 99–102 (1988).
Meares et al., *Br. J. Cancer*, 62, 21–26 (1990).
Gransow et al., ACS Symposium Series, No. 241, "Generator Produced Bi–212" (1984).
Moi et al., *Anal. Biochem.*, 148, 249–253 (1985).
Tweedle et al, Chemical Abstracts, 110(19), 173270, 1988.
Meares et al, Br. J. Cancer, 62, Suppl X, 21–21, 1990.
Deshpande et al, J. Nuclear Med. 4, pp473–479, Apr. 1990.

* cited by examiner

TETRA-AZA MACROCYCLES AND METAL COMPLEXES THEREOF

This is a continuation of application Ser. No. 07/372,348, filed Jun. 9, 1989, now abandoned which is a 371 of PCT/GB88/00671 filed Aug. 12, 1988.

FIELD OF THE INVENTION

This invention relates to functionalised tetra-aza macrocycles, to metal complexes thereof, to conjugate compounds containing the functionalised tetra-aza macrocycles and metal complexes thereof and to their use in diagnosis and therapy.

BACKGROUND TO THE INVENTION

The attachment of metal ions to proteins, peptides and other, smaller molecules is a fast expanding technology, which has numerous proven and potential applications in research, in industry and, particularly, in medicine.

In recent years, much of the impetus behind the development of this technology has been the ability to link metal ions to antibodies, especially monoclonal antibodies. Such metal labelled antibodies have found a widespread use, especially in medicine, where they have been employed, for example, to target the metal ion to a specific tissue type, both in vitro and in vivo. Thus, metal labelled antibodies have applications in locating specific tissue types (e.g. employing computer-aided tomographic techniques where the metal ion is in some way detectable) and in the treatment of cell disorders (e.g treating mammalian tumours where the metal ion is a cytotoxic radionuclide).

Conventionally, attachment of the metal ion to a protein such as an antibody has been achieved by complexation by an acyclic chelate such as a substituted diethylenetriaminepentaacetic acid [Gansow O. A. et al, Inorg. Chem., (1986), 25, 2772] or ethylenediaminetetraacetic acid [Meares, C. F. et al, Acc. Chem. Res., (1984), 17, 202] covalently linked to the antibody. Such acyclic complexes however tend to be unstable in vivo either as a result of acid-catalysed decomplexation or competitive chelate binding by $Ca^{2+}$ or $Zn^{2+}$ in serum, or as a result of competition from transferrin [Moerlein, S. M. et al, Int. J. Nuc. Med. Biol., (1981) 8, 277]. The lack of stability can result in uncomplexed metal atoms in the body which have a cytotoxic effect on healthy tissue (e.g. bone marrow) or which markedly reduce the signal-to-noise ratio of an imaging technique.

A possible alternative to the use of acyclic chelates in the labelling of antibodies is the use of macrocyclic ligands, which has been suggested in broad terms [Gansow O. A. et al. Am. Chem. Soc. Symp. Ser., (1984), 241, 215; UK Patent Specification Publication No. 2122641; and Moi M. K. et al, Anal. Biochem., (1985), 148, 249–253].

We have now found a new class of functionalised tetra-aza macrocyles, members of which are able to form more kinetically inert complexes with metal ions than are chelating agents conventionally in use for the attachment of metal ions to proteins and other molecules. The macrocycles of the invention are particularly useful for attachment to proteins, especially antibodies, to provide conjugate compounds capable of binding metals to give complexes which are advantageously stable in vivo.

SUMMARY OF THE INVENTION

Thus, according to one aspect of the present invention we provide a compound of general formula (1):

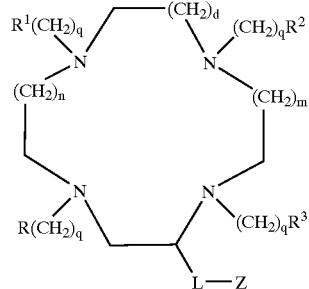

wherein m and n, which may be the same or different, is each zero or an integer 1, 2, or 3;

d is zero or an integer 1, 2 or 3;

q is zero or an integer from 1 to 6 inclusive;

R, $R^1$, $R^2$ and $R^3$, which may be the same or different, is each a hydrogen atom or an alkyl, alkoxyalkyl, —$CO_2H$, —$SO_3H$, —$PO_3H_2$ or aryl group;

L is a covalent bond or a linker group;

Z is a hydrogen atom or a reactive functional group, with the proviso that when L is a covalent bond Z is a reactive functional group;

and metal complexes and/or salts thereof.

In the compounds of formula (1), alkyl groups represented by R, $R^1$, $R^2$ and $R^3$ may be for example $C_{1-6}$alkyl groups such as methyl or ethyl groups. Alkoxyalkyl groups represented by R, $R^1$, $R^2$ or $R^3$ may be for example $C_{1-3}$alkoxy$C_{1-3}$alkyl groups e.g. methoxymethyl. When R, $R^1$, $R^2$ or $R^3$ is an aryl group it may be for example a substituted phenyl group, such as a group of formula

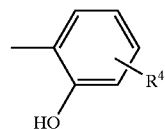

(where $R^4$ is a hydrogen atom or a $C_{1-6}$alkyl, e.g. methyl, $C_{1-3}$alkoxy$_{1-3}$alkyl, e.g. methoxymethyl, or $C_{6-12}$aryl, e.g. phenyl group).

In general, compounds of formula (1) in which R, $R^1$, $R^2$ and $R^3$ are the same are preferred. Compounds of this type in which q is an integer from 1 to 6 inclusive, particularly an integer 1, and $R^1$, $R^2$ and $R^3$ are —$SO_3H$, —$PO_3H_2$

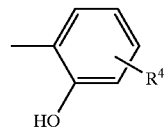

or, in particular, —$CO_2H$, are especially preferred.

In the compounds of formula (1), it will be appreciated that the nature of the group L when it is a linker group may be varied widely without substantially affecting the usefulness of compounds of formula (1) and the metal complexes thereof. Thus L may be any suitable organic radical and may be for example an optionally substituted aliphatic hydrocarbyl chain, optionally interrupted by one or more heteroatoms selected from —O— or —S— or by one or more —N($R^5$)— (where $R^5$ is a hydrogen atom or a $C_{1-6}$alkyl group), —CON(R$^5$)—, —N(R$^5$)CO—, cycloalkylene, aromatic, or heteroaromatic groups.

In the above definition, and in the same context whenever it appears below, the term "interrupted by" as applied to cycloaliphatic or aromatic groups is to be understood to also mean that these particular groups may additionally be present linked to the terminal carbon atom of the hydrocarbyl chain represented by L, at the opposite end of the chain to the carbon atom attached to the macrocycle.

Thus, for example, L may be an optionally substituted straight or branched $C_{1-20}$alkylene, $C_{2-20}$alkenylene, or $C_{2-20}$alkynylene chain, optionally interrupted by one or more —O— or —S— atoms or $C_{5-8}$cycloalkylene (e.g. cyclopentylene or cyclohexylene), $C_{6-12}$aromatic (e.g phenylene or substituted phenylene), $C_{5-10}$heteroaromatic (e.g furanyl, pyridyl), —N(R$^5$)—, —CON(R$^5$)— or —N(R)$^5$CO— groups.

Examples of substituents which may be present on the chain L include halogen atoms, e.g. fluorine, chlorine, bromine, or iodine atoms or groups selected from $C_{1-6}$alkoxy (e.g methoxy or ethoxy), hydroxy, nitro, —N(R$^6$)(R$^7$), [where R$^6$ is a hydrogen atoms or a $C_{1-6}$alkyl group and R$^7$ is a $C_{1-6}$alkyl group; e.g. —NHCH$_3$ or —N(CH$_3$)$_2$], or substituted amido, e.g. a group of formula —(CH$_2$)$_n$CON(R$^8$)(R$^9$) [where n is zero or an integer 1 to 4 inclusive, R$^8$ is a hydrogen atom or a $C_{1-6}$alkyl group, e.g. methyl and R$^9$ is an optionally substituted $C_{1-6}$alkyl group].

Substituted alkyl groups represented by R$^9$ include for example $C_{1-6}$alkyl groups substituted by one or more halogen atoms, or nitro, amino or hydroxy groups.

In general, in compounds of formula (1) the linker group is preferably an optionally substituted $C_{1-10}$alkylene, (especially $C_{1-6}$alkylene such as methylene, ethylene, propylene butylene, pentylene or hexylene) $C_{2-10}$alkenylene or $C_{2-10}$alkynylene chain optionally interrupted by one or more —O— or —S— atoms or cyclohexylene, phenylene, substituted phenylene, —NH—, —N(CH$_3$)—, —CONH—, —CON(CH$_3$)— —NHCO— or —N(CH$_3$)CO— groups.

Particular examples of linker groups represented by L include, for example, —(CH$_2$)$_d$— (where d is an integer 1 to 4 inclusive),

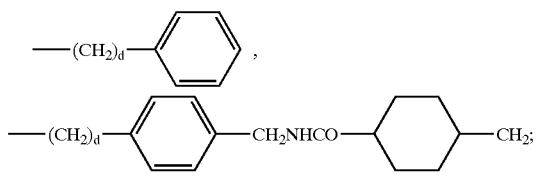

—(CH$_2$)$_d$NHCO(CH$_2$)$_e$— (where e is an integer 1 to 4 inclusive) and —(CH$_2$)$_d$NHCO(CH$_2$)$_e$OCH$_2$—.

The reactive functional group represented by Z in compounds of formula (1) may be any group capable of reacting with a thiol, amino, carboxyl, hydroxyl, aldehyde, aromatic or heteroaromatic group. Aromatic groups include, for example, phenolic groups. Heteroaromatic groups include for example imidazolyl groups.

Thus, Z may be, for example,
(i) a halogen atom (as for example a chlorine, bromine or iodine atom),
(ii) a group selected from —SH, —NH$_2$, hydrazino (—NHNH$_2$) or a derivative thereof, (for example —N(CH$_3$)NH$_2$, —NHCONHNH$_2$, —NHCSNHNH$_2$, or phenyl hydrazino),
(iii) —NCO, —NCS, —COR$^{10}$ in which R$^{10}$ is a halogen atom (as for example a chlorine or bromine atom), N$_3$, $C_{1-6}$alkoxy, (as for example methoxy), $C_{6-12}$aryloxy (as for example nitrophenyloxy or dinitrophenyloxy), imidyloxy (as for example succinimidyloxy) or imidazolyloxy,
(iv) imido, (as for example maleimido), or
(v) a vinyl group of the formula —Het$^1$—C(R$^{12}$)=CH$_2$ in which
Het$^1$ and R$^{12}$, which may be the same or different, are each a nitrogen containing heterocyclic group, (as for example a pyridyl group) or
Het$^1$ is a nitrogen containing heterocyclic group and R$^{12}$ is a hydrogen atom
as for example a vinyl pyridyl group of formula:

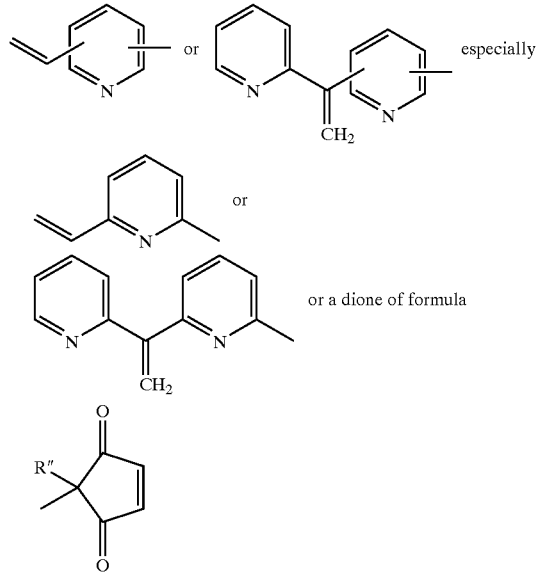

or a dione of formula (where R$^{11}$ is a $C_{1-4}$alkyl e.g. methyl, group).

Metal complexes of the compounds of formula (1) include complexes wherein the metal is di- or tripositive and has a coordination number 6 or greater, especially 8. Examples of such metals include indium (In), copper (Cu), lead (Pb), bismuth (Bi), yttrium (Y), terbium (Tb), gadolinium (Gd) and Scandium (Sc). Y, Pb, Tb, Gd, and Sc are preferred, particularly Y, Gd and Pb. In general the metal is preferably a radioactive isotope. Yttrium, especially $^{90}$Y, is particularly preferred.

In general, optimum binding of the metal to the compounds of formula (1) may be achieved by selection of the ring size and where appropriate by adjusting the potential coordination number by choice of the group (CH$_2$)$_q$R, —(CH$_2$)$_q$R$^1$, —(CH$_2$)$_q$R$^2$, and/or —(CH$_2$)$_q$R$^3$ Thus a particularly important class of compounds of formula (1) is that wherein d is an integer 1. Especially useful compounds are those wherein d is an integer 1, m is an integer 1 or 2 and n is an integer 1 or 2. In general, compounds of formula (1) in which —(CH$_2$)$_q$R, —(CH$_2$)$_q$R$^1$, —(CH$_2$)$_q$R$^2$ and —(CH$_2$)$_q$R$^3$ is each —CH$_2$CO$_2$H are particularly useful.

Salts of the compounds of formula (1) include salts with bases, e.g. sodium or potassium salts, or acid addition salts such as hydrobromides or hydrochlorides. Pharmaceutically acceptable salts are particularly preferred.

A particularly useful group of compounds of the invention has the formula (1) wherein R, R$^1$, R$^2$, R$^3$, m, n, d ,and q are as defined for formula (1) and the groups —L and Z together represent a group —(CH$_2$)$_r$—X—Y in which     (1)

r is zero or an integer from 1 to 6 inclusive,
X is:
—NH—,

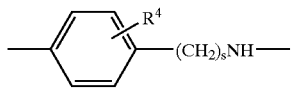

in which $R^4$ is as previously defined and s is zero or an integer from 1 to 4 inclusively,
—$(CH_2)_s$NHNH—, or
—$(OCH_2CH_2)_t$NH— in which t is an integer from 1 to 6 inclusively, and
Y is a group —$COZ^1$ or —$CO(R)Z^1$ in which
R is a spacer group, and
$Z^1$ is a group —$(CH_2)_r$Hal in which Hal is a halogen atom;

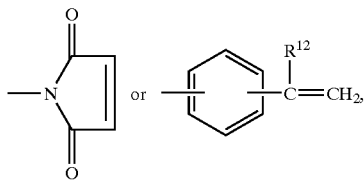

where $R^{12}$ is hydrogen or a nitrogen containing aromatic heterocyclic group, as for example a pyridyl group, or —$(CH_2)_r$NCS;                  (2)

and the metal complexes and/or salts thereof.

In compounds of this type, the spacer group R may be for example an alkylene, e.g. ethylene, alkoxyalkylene, e.g. methoxymethylene, aryl, e.g. phenylene, aralkylene, e.g. phenalkylene such as phenethylene, or cycloalkylalkylene, e.g. cyclohexylmethylene group.

A further particularly useful group of compounds according to the invention has the formula (1) wherein R, $R^1$, $R^2$, $R^3$, m, n, d and q are as defined for formula (1) and the groups L and Z together represent a group —$(CH_2)_r$XH (where r and X are as defined above) and the metal complexes and/or salts thereof.

An important group of compounds according to the invention has the formula (1a):

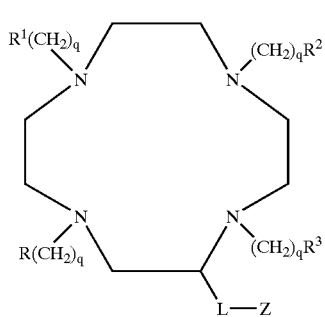

(1a)

wherein R, $R^1$, $R^2$, $R^3$, L and Z are as defined for formula (1) and metal complexes ad/or salts thereof.

Compounds of this type in which R, $R^1$, $R^2$ and $R^3$ is each —$CO_2H$ are particularly preferred.

Compounds of formula (1a) in which L is a linker group [particularly those specifically identified for compounds of formula (1)] are especially useful.

Z in compounds of formula (1a) is preferably a reactive functional group, particularly those specifically identified for compounds of formula (1), especially a group of formula —$Het^1$—$CR^{12}$=CH or a dione of formula

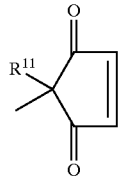

Yttrium complexes of the compounds of formula (1a) are particularly useful.

Yttrium complexes of the compounds of formula (1a) are particularly useful.

The compounds of formula (1) and the metal complexes and/or salts thereof have a diagnostic use as imaging agents in vitro and in vivo. The compounds of formula (1) and the metal complexes and/or salts thereof are also cytotoxic agents and may be used in the treatment of abnormal cell disorders, for example in the treatment of tumours.

For application of the compounds of formula (1) as imaging or cytotoxic agents, it is generally preferable to couple the compounds to other molecules such as proteins, especially antibodies, peptides or carbohydrates to form conjugate compounds, and the compounds of formula (1) are particularly well adapted for use in this respect.

Thus, according to a further aspect of the invention, we provide a conjugate compound which comprises a compound of formula (1), or a metal complex and/or salt thereof, coupled to a protein, peptide or carbohydrate.

The compound of formula (1) may be coupled through any thiol, amino, carboxyl, hydroxyl, aldehyde, aromatic or heteroaromatic group present in the protein, peptide or carbohydrate.

In a preferred aspect of the invention, we provide a conjugate compound which comprises a compound of formula (1) or a metal complex and/or salt thereof, coupled to an antibody.

It is to be understood that conjugate compound according to the invention may contain more than one molecule of a compound of formula (1) coupled to any one protein, peptide or carbohydrate molecule.

In a particular aspect, the invention provides a conjugate compound of formula

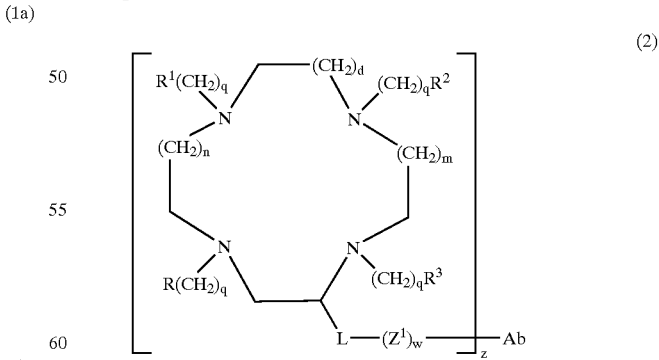

(2)

wherein m, n, d, q, R, $R^1$, $R^2$, $R^3$, and L are as defined for formula (1);

$Z^1$ is the residue of a reactive functional group;

w is zero or an integer 1;

z is an integer 1 or more;

Ab is an antibody; and metal complexes and/or salts thereof.

In the compounds of formula (2), the residue of a reactive functional group represented by $Z^1$ may in general be the residue of a reactive functional group Z as defined for formula (1).

In particular, $Z^1$ may be for example —S—, —NH—, —NHN=, N(CH$_3$)N=, —NHCONHN=, —NHCSNHN=, —N(Ph)N= in which Ph is phenyl, —NC(O)—, —NC(S)—, —CO—,

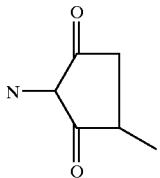

—Het$^1$—C(R$^{12}$)CH$_2$— or

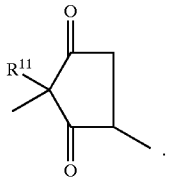

The antibody Ab in the conjugates of formula (2) may be a complete antibody molecule or a fragment thereof, or an analogue or either of these, provided that the antibody comprises of a specific binding region. Thus the antibody may be polyclonal, or, preferably, monoclonal, or a fragment thereof for example a Fab' or F(ab)$_2$' fragment. If desired the antibody may be a recombinant antibody, (i.e. an antibody which has been produced using recombinant DNA techniques). The antibody may be a chimaeric antibody comprising linked antibody fragments, each from a different source (see for example International Patent Specification No. WO 86/01533).

The antibody may be specific for any number of antigenic determinants, but is preferably specific for one antigenic determinant. Particular determinants include tumour cell-associated antigens, particularly mammalian tumour cell antigens for example oncofetal antigens such as carcinoembryonic antigen or alphafetoprotein.

A particular useful antibody is that known as B72.3 [Colcher, D. et al Proc. Nat. Acad. Sci. USA (1981), 78, 3199].

The antibody Ab will in general be coupled to the remainder of the conjugate of formula (2) (i.e. the macrocycle and linker) through any appropriate reactive atom or group, for example a nitrogen or, especially, sulphur atom, present in the antibody. It will be appreciated that any one antibody molecule may contain more than one reactive group capable of coupling with the macrocycle and linker. Thus, for example, z in the conjugates of formula (2) may be an integer 1, 2, 3, 4, 5, 6 or more depending on the number of macrocycles linked to any particular antibody molecule or fragment or analogue thereof.

Yttrium complexes of conjugates of formula (2) are particularly useful.

It is to be understood that the definitions and preferences expressed for m, n, d, q, R, R$^1$, R$^2$, R$^3$ and L in compounds of formula (1), and for classes of compounds of formula (1) are also applicable to conjugates of formula (2).

Particularly useful conjugate compounds according to the invention are those comprising a compound of formula (1a), or a metal complex and/or salt thereof, coupled to an antibody. The indium complexes of these conjugates are especially important.

The compounds of formulae (1) and (2) may be formulated for use in accordance with conventional practice, and thus according to a further aspect of the invention we provide a composition comprising a compound of formula (1) or a compound of formula (2) or a metal complex and/or salt thereof, together with one or more pharmaceutically acceptable carriers.

Particularly suitable compositions according to the invention are those adapted for parenteral administration, especially intravenous administration. Suitable formulations of this type include solutions of the compounds of formulae (1) or (2) in isotonic saline.

The quantities of compounds of formulae (1) or (2) used in formulations according to the invention will vary according to the intended use (i.e. imaging or therapy) and other variables such as the intended cell target, but may be easily determined in accordance with conventional practice for reagents of this type.

Compounds of the invention may be prepared by the following processes wherein the groups and symbols R, R$^1$, R$^2$, R$^3$, m, n, d, q, L, Z, Ab and z are as defined for formulae (1) and (2) except where stated otherwise. Where a metal complex is desired as a final product, the complexation with a metal atom may be carried out as a final step in the production process, as described below for the complexation of compounds of formulae (1), or alternatively it may be desirable to complex the metal at an earlier stage in the process, providing of course that the requisite macrocycle structure is present. In the following processes, it may be desirable to use starting materials in which the group Z is in a protected state, or which contain a precursor of the group, as discussed below.

Thus, according to a further aspect of the invention a compound of formula (1) or a metal complex thereof may be prepared by reaction of a corresponding compound of formula (3)

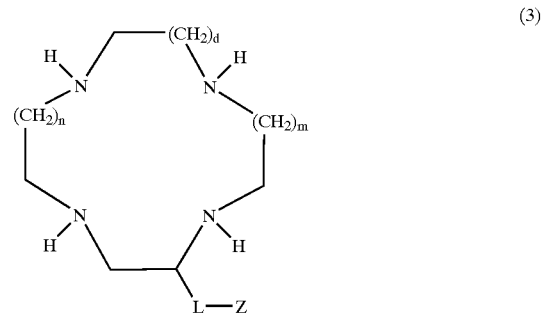

or a metal complex thereof, with a reagent R$^1$(CH$_2$)$_q$D (where D is a displaceable group). Displaceable groups represented by D include for example halogen atoms, for example a bromine, chlorine or iodine atom.

The reaction may be performed in a solvent such as water or an organic solvent such as a nitrile e.g. acetonitrile or an alcohol e.g. isopropanol or an amide e.g. dimethylformamide in the presence of a base, e.g. an inorganic base such as an alkali metal carbonate or hydroxide, e.g. sodium, potassium or caesium carbonate, or sodium, potassium or lithium hydroxide, at a high temperature e.g. the reflux temperature.

In this reaction, the group Z may need to be in a protected state. Conventional protecting groups may be used, depending on the nature of Z, and may be removed using standard procedures, once the desired reaction has been effected. Similarly, when the reagent $R^1(CH_2)_qD$ contains an acid group this may also need to be protected, for example as an ester e.g. a methyl ester. The acid may be re-generated after the desired reaction is complete, for example by hydrolysis using an acid such as sulphuric acid.

It will be appreciated that where it is desired to prepare a compound of formula (1) in which R, $R^1$, $R^2$ and $R^3$ are not the same this may be achieved by first selectively N-protecting the compound of formula (3) or a precursor using an appropriate amine protecting group(s), for example a p-toluenesulphonyl group as described below, in accordance with conventional practice. Reaction of the N-protected compound (3) with $R^1(CH_2)_qD$ followed by deprotection and further reaction as necessary with other reagents $R^1(CH_2)_qD$ then yields the desired compound in which R, $R^1$, $R^2$ and $R^3$ are not the same.

Where metal complexes of compounds of formulae (1) or (2) are required (or any other suitable macrocyclic intermediate described herein) these may be prepared by treating the compound with a metal salt (for example a metal halide) in an appropriate solvent for example an aqueous or non aqueous solvent, (e.g. acetonitrile, acetone, propylene carbonate, dimethylformamide or dimethylsulphoxide) at any suitable temperature from 0° C. to 100° C. such as 10° to 80° C. e.g. around 60° C.

In another process, a compound of formula (1) or a metal complex thereof wherein R, $R^1$, $R^2$ and $R^3$ is each —$(CH_2)_q$PO$_3$H$_2$ (where q is an integer 1 to 6) may be prepared by reaction of a compound of formula (3) or a metal complex thereof with phosphorous acid and an aldehyde $R^bCHO$ (where $R^b$ is a hydrogen atom or a $C_{1-5}$alkyl group) in the presence of an acid, such as hydrochloric acid at an elevated temperature, e.g. 100°–130° C.

Compounds of formula (1) may also be prepared by interconversion from other compounds of formula (1). Thus one functional group Z may be exchanged for another and, if desired a linker group L changed to another by appropriate manipulative reactions. For example, a compound of formula (1) where —L—Z is a group —$L^1$—NHCO—$L^2$—Z (where —$L^1$—NHCO—$L^2$ represents the group L) may be prepared by reaction of a corresponding compound wherein —L—Z represents —$L^1$—NH$_2$ with a reagent $R^bO$—$L^2$—Z (where $R^b$ is for example an imide, such as succinimide, or a substituted phenyl group such as a p-nitrophenyl group) in the presence of a tertiary amine, such as diisopropylethylamine, in a solvent such as dimethylformamide.

Reagents of formula $R^bO$—$L^2$—Z are either known compounds or may be obtained form known starting materials using methods analogous to those used for the preparation of the known compounds.

A conjugate compound of formula (2) or a metal complex thereof may be prepared by reaction of a corresponding compound of formula (1) or a metal complex thereof with an antibody Ab (as previously defined).

The reaction may be performed in a suitable solvent, for example an aqueous solvent such as a phosphate buffer, at an appropriate temperature, for example at 0°–30° C., especially 0°–10° C. e.g. 4° C.

The antibody Ab may be obtained using procedures well known in the art. If desired, before the coupling reaction, the antibody may first be treated to yield appropriate groups for reaction with the compound of formula (1). Thus for example the antibody may be subjected to oxidation, for example periodate oxidation to yield aldehyde groups, or, in particular, may be treated with a reagent [e.g. Traut's reagent (2-iminothiolane)] using standard procedures to generate free sulphydryl groups in the molecule.

Salts of compounds of formulae (1) or (2) and their metal complexes may be prepared by conventional means, for example by reaction with an appropriate base or acid in a suitable aqueous solvent.

Intermediates of formula (3) may be prepared by deprotection of a compound of formula (4)

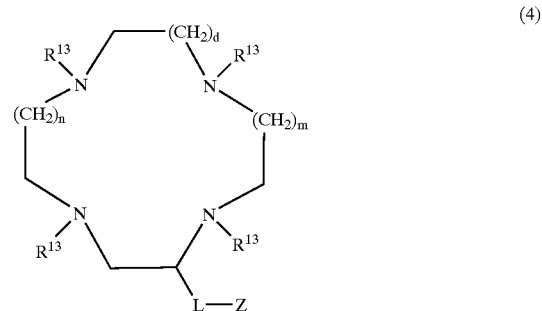

(4)

(where $R^{13}$ is a protecting group such as a p-toluenesulphonyl group. The deprotection will depend on the nature of the protecting group $R^{13}$. Thus, for example, when $R^{13}$ is a p-toluenesulphonyl group removal of this may be achieved by treatment of the compound of formula (4) with an acid, for example HBr-acetic acid, in the presence of phenol at a high temperature, or by reaction with lithium in liquid ammonia in the presence of an alcohol such as ethanol.

Intermediates of formula (4) may be prepared by treating a compound of formula (5)

$R^{13}NH(CH_2)_nCH_2N(R^{13})CH_2CH(L—Z)N(R^{13})CH_2(CH_2)_mNHR^{13}$ with a compound $R^{13}OCH_2(CH_2)_dOR^{13}$ in the presence of a base such as sodium ethoxide in a solvent such as dimethylformamide.

Intermediates of formula (5) may be prepared by reaction of compounds of formula (6)

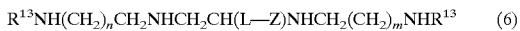

$R^{13}NH(CH_2)_nCH_2NHCH_2CH(L—Z)NHCH_2(CH_2)_mNHR^{13}$ (6)

with a protecting agent, for example p-toluenesulphonyl chloride in a base such as pyridine.

Intermediates of formula (6) in which m and n are the same may be prepared by reaction of a diamine of formula (7):

$H_2NCH(L—Z)CH_2NH_2$ (7)

with a reagent $R^{13}NH(CH_2)_mCOHal$ (where Hal is a halogen atom) in the presence of a base such as triethylamine, followed by reduction using for example borane in a solvent such as tetrahydrofuran at a high temperature e.g. the reflux temperature, followed by treatment with an acid such as hydrochloric acid.

Where it is desired to prepare an intermediate of formula (9) in which m and n are not the same a protected amine $H_2NCH(L—Z)CH_2NHR^{13}$ may be used in the above reaction. Removal of the protecting group after the reaction followed by repeated alkylation with a different compound $R^{13}NH(CH_2)_nCOHal$ then yields the required intermediate.

Diamines of formula (7) may be prepared from an appropriately substituted amino acid of formula (8):

by reaction with ammonia in a solvent such as methanol, followed by reduction using for example lithium aluminium hydride.

The substituted amino acids of formula (8) are either known compounds or may be prepared using methods analogous to those used for the preparation of the known compounds.

In an alternative process, intermediates of formula (5) may be prepared by reaction of a compound of formula (9)

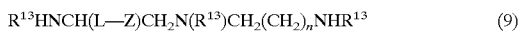

with a compound $R^{13}OCH_2(CH_2)_dN(R^{13})(CH_2)_mCH_2OR^{13}$ in the presence of a base such as caesium carbonate in a solvent such as dimethylformamide.

Intermediates of formula (9) may be prepared by reduction of compounds of formula (10)

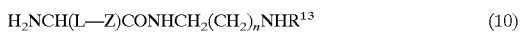

using for example borane as described above, followed by reaction to introduce the protecting group $R^{13}$, for example with p-toluenesulphonyl chloride in a solvent such as dichloromethane in the presence of a base such as triethylamine at e.g. reflux.

Intermediates of formula (10) may be prepared by reaction of an appropriately substituted amino acid of formula (8) (where $R^{11}$ is a methyl or ethyl group) with a diamine $H_2NCH_2(CH_2)_nNH_2$ at a high temperature, e.g. the reflux temperature.

The invention is illustrated by the following Examples.

DESCRIPTION OF SPECIFIC EMBODIMENTS

Intermediate 1

2,6-Diamino-1-hexanoic acid, ethylenediamine ester 2,6-Diamino-1-hexanoic acid, methyl ester, dihydrochloride (10.283 g) was added (as solid) in small batches over a 50 minute period to ethylenediamine (100 ml) at 90° C., with stirring. The temperature of the reaction mixture was then raised to 140° C. for 6 hrs, after which the ethylenediamine was removed by vacuum distillation to yield a brown residual oil which was taken up in 4M NaOH (25 ml) and dried in vacuo. Methanol (30 ml) was added, the solution was filtered, the methanol removed (Buchi) and the residue dissolved in $CH_2Cl_2$ (100 ml), then filtered, and the filtrate rotovated down to give the title compound as a clear brown oil (8.827 g). i.r (thin film) 3300/3280 3060 2930 2860 1650 1570 1470 1320 cm$^{-1}$.

Intermediate 2

1,5,9-Triamino-3-aza-nonane, tetrahydrochloride

Intermediate 1 (3.754 g) and borane-tetrahydrofuran (130 mmol, 130 ml) was refluxed for 21 hours. After removal of volatiles, the aminoborane was washed with methanol (2×100 ml) and hydrolysed with 6M HCl (150 ml, 110° C.) for 3 hours. The resulting solution was evaporated, methanol (20 ml) added and further evaporated to yield the title compound (6.279 g) as a white hygroscopic solid.

Intermediate 3

1,5-Diamino-(9-N-benzamidy)1-3-aza-nonane

Intermediate 2 (6.16 g) and potassium hydroxide (4.4 g) was dissolved in water (50 ml) and, with stirring, copper carbonate (2.603 g) was added. Continued stirring over 30 minutes at 50° C. yielded an intense blue solution which was cooled to 0° C. and benzoyl chloride 2.5 ml added in 0.25 ml portions over 90 minutes keeping the pH greater than 9 with periodic addition of KOH pellets. The solution was then allowed to stir at room temperature for 1 hour, then filtered and the filtrate treated with $H_2S$ over 30 minutes. The solution was filtered once again to give a greeny-yellow filtrate which on addition of KOH to pH14 went a dark green, with a small amount of green precipitate. This was filtered off, the filtrate reduced in volume to 40 ml and exhaustively extracted (13×) with $CH_2Cl_2$, dried ($K_2CO_3$), and evaporated to yield the title compound as a pale yellow oil (2.152 g). $^1$H-NMR (250 MHz), δ(CDCl$_3$): 1.57 (m, 16H, $CH_2$, NH, NH$_2$) 2.37 (dd, 1H, CH), 2.67 (m 3H, $CH_2$N), 2.79 (m, 3H, $CH_2$N).

Intermediate 4

1,5-Ditosylamino-3-tosyl-(9-N-benzamidyl)-3-aza-nonane

Intermediate 3 (1.978 g) in dry $CH_2Cl_2$ (50 ml) was added dropwise to a solution of tosyl chloride (5.087 g), in dry $CH_2Cl_2$ (50 ml) and the mixture was then allowed to stir for 2½ hours at room temperature. The solution was then washed with water (20 ml) dried ($K_2CO_3$), filtered and evaporated to an oily brown residue which was redissolved in $CH_2Cl_2$ (10 ml). After a few minutes a white solid precipitated which was collected by filtration and washed with $CH_2Cl_2$ to give the title compound (1.701 g).

TLC (silica; 5% methanol in $CH_2Cl_2$) Rf 0.44 m/e [desorption chemical ionisation (methanol)] 741 (M$^+$+1), 740 (M$^+$).

Intermediate 5

2-(4-N-Benzamidyl)butyl-N,N',N",N'"-tetratosyl-1,4,7,10-tetrazacyclododecane

Intermediate 4 (1.116 g) was dissolved in anhydrous dimethylformamide (100 ml) and caesium carbonate (1.032 g) added under dry nitrogen. A solution of TsO(CH$_2$)$_2$N(Ts)(CH$_2$)$_2$OTs(0.855 g; where Ts represents tosyl), in anhydrous dimethylformamide (40 ml) was slowly added, with stirring, over 3 hours. Stirring was continued at room temperature for 20 hours. The dimethylformamide was removed under reduced pressure and the residue dissolved in chloroform (200 ml), washed with water (3×30 ml) and dried ($K_2CO_3$) to yield the title compound. m/e [desorption chemical ionisation (iso-but)]: 964 (M$^+$+1), 963 (M$^+$).

Intermediate 6

2-(4-N-Benzamidyl)butyl-1,4,7,10-tetrazacyclododecane

To Intermediate 5 (0.499 g) in a flask under nitrogen was added ethanol (2 ml), and liquid ammonia (100 ml) then allowed to condense in the flask. Lithium metal (0.18 g) was added and an intense blue colour developed which discharged within 20 minutes. After evaporation of NH$_3$ (3 hours) water (20 ml) was added and the solution evaporated to dryness, taken up in 6 MHCl (20 ml) washed with ether (3×20 ml), evaporated to dryness and redissolved in 6M KOH (20 ml) and extracted with dichloromethane (5×20 ml). The extract was dried ($K_2CO_3$) and evaporated to yield the title compound (0.115 g). m/e [desorption chemical ionisation (methanol)]: 348 (M$^+$+1).

EXAMPLE 1

2-[4-(6-Ethenylpyrid-2-ylmethoxyacetamido)butyl]-1,4-7,10-tetrazacyclododecane-1,4,7,10-tetraacetic acid (a) 2-(4-N-Benzamidylbutyl)-1,4,7,10-tetrazacyclododecane-1,4,7,10-tetraacetic acid (a) Intermediate 6 (75 mg) was dissolved in dry dimethylformamide (3 ml) and $K_2CO_3$ (146 mg) added, followed by methylbromoacetate (160 mg). The mixture was heated to 90° C. for 6 hours under nitrogen, further $K_2CO_3$ (30 mg) and methylbromoacetate (32.3 mg) were added and the heating continued at 90° C. for a further 12 hours under nitrogen. The mixture was filtered and water (3 ml) added followed by lithium hydroxide monohydrate (50 mg). The reaction was monitored by reverse phase high performance liquid chromatography (RPHPLC-conditions given below) and two new products were formed (T=10.7 and 11.5 minutes). More lithium hydroxide monohydrate (50 mg) was added and the reaction went to completion, the predominant product by RPHPLC eluting at 10.7 minutes. The reaction mixture was concentrated in vacuo to give a brown oil which was purified on DEAE Sepharose using a gradient elution of 25 mM ammonium acetate (pH=5.6)/10% $CH_3CN$ up to 1.0M ammonium acetate (pH5.6)/10% $CH_3CN$. The appropriate fractions were pooled and concentrated in vacuo to give the title compound (47 mg) of Part (a) as a white solid. m/e (Fab, glycerol) 580 (M+H$^+$).

RPHPLC CONDITIONS:

| Column: | Sperisorb SODS2 (25 cm × 0.4 mm) |
|---|---|
| Flow Rate: | 1.4 ml/minute |
| Solvents: | A = 0.1% trifluoroacetic acid/$H_2O$ |
| | B = 0.1% trifluoroacetic acid/$CH_3CN$ |
| | λ = 254 nm |

| TIME (T: minutes) | % A | % B |
|---|---|---|
| 0 | 95 | 5 |
| 20 | 5 | 95 |
| 20.1 | 95 | 5 |

(b) 2-(4-Aminobutyl)-1,4,7,10-tetrazadodecane-1,4,7,10-tetraacetic acid

The compound of Part (a) [37 mg] was dissolved in 6M HCl (10 ml) and heated to 140° C. for 16 hours under nitrogen. The reaction mixture was concentrated in vacuo and coevaporated with dry dimethylformamide (3×10 ml) to yield the title compound of Part (b) which was used in the following reaction without further purification.

(c) 2-[4-(6-Ethenylpyrid-2-ylmethoxyacetamido)butyl]-1,4-7,10-tetrazacyclododecane-1,4,7,10-tetraacetic acid The amine prepared in Part (b) was dissolved in dry dimethylformamide (10 ml) and diisopropylethylamine (10 mg) was added followed by the p-nitrophenyl ester of 2-vinyl-6-methoxyacetic acid pyridine (24 mg). The reaction was monitored using ion exchange chromatography (A×100—conditions given below) and a new product was observed at T=13.3 minutes. Extra addition of the nitrophenyl ester/diisopropylethylamine did not give any increase in product and the reaction mixture was ninhydrin negative. The mixture was then concentrated in vacuo and water added followed by $CH_2Cl_2$. The aqueous layer was extracted with $CH_2Cl_2$ (3×20 ml) and concentrated in vacuo. The residue was chromatographed on DEAE Sepharose eluting with 25 mM up to 500 mM ammonium acetate/$CH_3CN$ (9:1) pH5.6. The appropriate fractions were pooled and concentrated in vacuo to give the title compound (20 mg) as a white solid. m/e (FAB, glycerol) 651 (M$^+$+1).

A×100 (Synchropak–25 cm×0.4 mm) ion exchange chromatography:

A=$H_2O$; B=1M ammonium acetate, pH5.6: C=$CH_3CN$.

Flow Rate=1.4 ml/minute; λ=254 nm.

| TIME (T; minutes) | % A | % B | % C |
|---|---|---|---|
| 0 | 70 | 10 | 20 |
| 20 | 10 | 80 | 20 |
| 20.1 | 70 | 10 | 20 |

Title Compound elutes at 13.3 minutes.

What is claimed is:

1. A compound 1,4,7,10-tetrazacyclododecane of the formula:

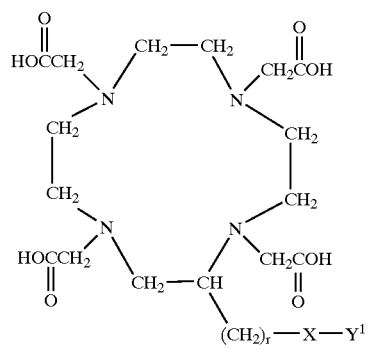

wherein r has a value of from 0 to 6;

X is

—NH—

—$(CH_2)_s$NHNH—, or

—$(OCH_2CH_2)_t$—NH— in which s has a value of from 0 to 4 and t has a value of from 1 to 6; and $Y^1$ is capable of reacting with an antibody and is selected from the group consisting of —$COZ^1$, or —$CO(R)Z^1$ in which $Z^1$ is maleimido,

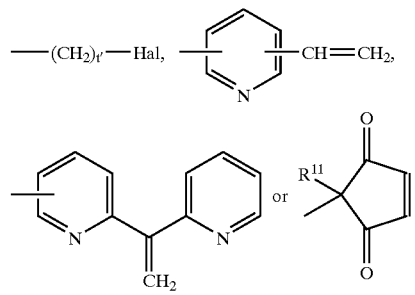

Hal is a halogen atom;

R is alkylene, phenylene, phenethylene, or cyclohexylmethylene;

$R^{11}$ is alkyl of 1 to 4 carbon atoms; and t' has a value of from 1 to 6.

2. A compound according to claim 1 wherein $Z^1$ is maleimido, 6-vinylpyridin-2-yl, or 6-[1-(pyrid-2-yl)ethenyl]pyridin-2-yl.

3. A compound consisting of:

1,4,7,10-tetrazacyclododecane of the formula:

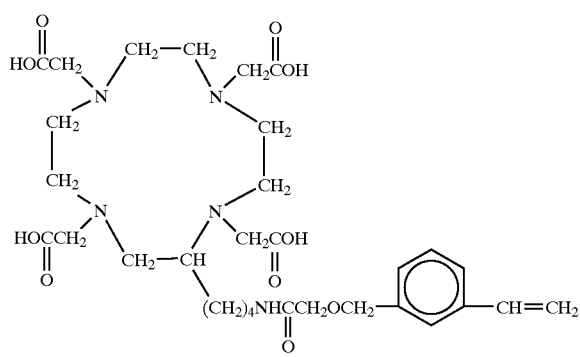

4. A conjugate comprising 1,4,7,10-tetrazacyclododecane of the formula:

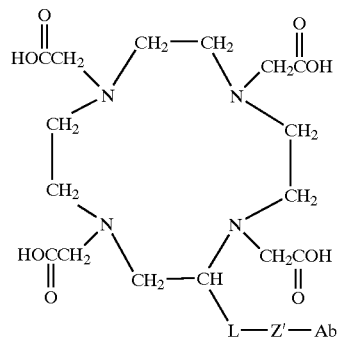

wherein

L is an aliphatic hydrocarbon chain interrupted at a point other than that of attachment to the depicted 1,4,7,10-tetrazacyclododecane ring by one or more members selected from the group consisting of —O—, —S—, —N($R^5$)—, —CON($R^5$)—, —N($R^5$)CO—, a cycloalkylene ring, and a pyridine ring, in which $R^5$ is hydrogen or alkyl of 1 to 6 carbon atoms;

Z' is the residue of a group capable of reacting with a site on an antibody, and Ab is a monoclonal or polyclonal antibody or antibody fragment.

5. A composition comprising a compound according to claim 1 and a pharmaceutically acceptable carrier.

6. A composition comprising a conjugate according to claim 4 and a pharmaceutically acceptable carrier.

* * * * *